(12) United States Patent
Nakar et al.

(10) Patent No.: US 11,771,373 B2
(45) Date of Patent: Oct. 3, 2023

(54) STAGGERED ELECTRODE ARRANGEMENTS FOR ELECTROPHYSIOLOGICAL SENSING

(71) Applicant: BIOSENSE WEBSTER (ISRAEL) LTD., Yokneam (IL)

(72) Inventors: Elad Nakar, Timrat (IL); Yoav Benaroya, Kfar Saba (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 362 days.

(21) Appl. No.: 17/092,627

(22) Filed: Nov. 9, 2020

(65) Prior Publication Data
US 2022/0142578 A1 May 12, 2022

(51) Int. Cl.
*A61B 5/05* (2021.01)
*A61B 5/00* (2006.01)
*A61B 5/24* (2021.01)

(52) U.S. Cl.
CPC .............. *A61B 5/6853* (2013.01); *A61B 5/24* (2021.01); *A61B 5/6859* (2013.01); *A61B 2562/046* (2013.01); *A61B 2562/166* (2013.01)

(58) Field of Classification Search
CPC ...... A61B 18/1492; A61B 2018/00214; A61B 2018/0016; A61B 2018/0022; A61B 2018/1467; A61B 2018/00267; A61B 5/287; A61B 2018/126; A61B 2018/1435; A61B 2018/1475; A61B 2018/1465; A61B 5/6852; A61B 2018/00285; A61N 1/05; A61N 1/04

USPC ........ 600/372–374, 377, 381, 393, 434–435, 600/508–509; 604/96.01, 192; 606/20–52; 607/115–116, 119

See application file for complete search history.

(56) References Cited

U.S. PATENT DOCUMENTS

| | | | |
|---|---|---|---|
| 4,522,212 A * | 6/1985 | Gelinas | A61N 1/368 600/374 |
| 5,391,199 A | 2/1995 | Ben Haim | |
| 5,443,489 A | 8/1995 | Ben Haim | |
| 5,558,091 A | 9/1996 | Acker | |
| 5,873,849 A | 2/1999 | Bernard | |
| 5,944,022 A | 8/1999 | Nardella | |
| 5,983,126 A | 11/1999 | Wittkampf | |
| 6,177,792 B1 | 1/2001 | Govari | |
| 6,456,864 B1 | 9/2002 | Swanson | |
| 6,690,963 B2 | 2/2004 | Ben Haim | |
| 6,788,967 B2 | 9/2004 | Ben Haim | |
| 7,536,218 B2 | 5/2009 | Govari | |
| 8,456,182 B2 | 6/2013 | Bar-Tal | |

(Continued)

FOREIGN PATENT DOCUMENTS

| | | |
|---|---|---|
| CN | 201375515 Y | 1/2010 |
| CN | 209003993 U | 6/2019 |

OTHER PUBLICATIONS

European Search report for corresponding EPA No. 21206987.6 dated Apr. 8, 2022.

*Primary Examiner* — Joseph A Stoklosa
*Assistant Examiner* — Brian M Antiskay

(57) ABSTRACT

An apparatus includes a shaft, configured for insertion into a body of a subject, and an expandable element coupled to a distal end of the shaft. The expandable element includes multiple electrodes arranged in a hexagonal grid when the expandable element is expanded. Other embodiments are also described.

5 Claims, 4 Drawing Sheets

(56) References Cited

U.S. PATENT DOCUMENTS

| | | |
|---|---|---|
| 2016/0317094 A1 | 11/2016 | Byrd |
| 2016/0374753 A1* | 12/2016 | Wu ................ A61B 5/6859 606/41 |
| 2018/0116539 A1 | 5/2018 | Olson |
| 2018/0117309 A1 | 5/2018 | Rapoport |
| 2019/0110750 A1 | 4/2019 | Dahlen |
| 2019/0159835 A1 | 5/2019 | Ibrahim |
| 2019/0239765 A1 | 8/2019 | Fuentes-Ortega |

\* cited by examiner

STAGGERED ELECTRODE ARRANGEMENTS FOR ELECTROPHYSIOLOGICAL SENSING

FIELD OF THE INVENTION

The present invention relates to intrabody electrophysiological sensing.

BACKGROUND

U.S. Pat. No. 5,873,849 describes electrodes and electrode array apparatus and systems for in vivo delivery of electrical waveforms by utilizing an electrode array having at least three individually addressable electrodes disposed so as to form a triangle in a plane intersecting the electrodes and an electrical signal generating device operatively connected to the electrodes for delivering electrical waveforms to said electrodes and generating electroporation-inducing electrical fields between the electrodes.

US Patent Application Publication No. 2016/0317094 describes an electrophysiology system for mapping tissue, including a catheter having a plurality of electrodes. The system may be a catheter having a dense collection of small electrodes on its tip. The electrodes may be arranged in a pattern that is constant regardless of rotational orientation. The system may be an electrophysiology apparatus having a catheter, the catheter having a body with a proximal end and a distal end. At the distal end of the catheter body is a distal tip comprising a plurality of electrodes and/or coaxtrodes. A signal processor may be operably connected to the plurality of electrodes and/or coaxtrodes and can measure at least one electrophysiological parameter.

US Patent Application Publication No. 2019/0239765 describes an electrophysiology catheter with a distal electrode assembly having a covered spine carrying a plurality of microelectrodes. The position of the microelectrodes on each spine is staggered relative to microelectrodes on adjacent spines so as to minimize the risk of electrodes on adjacent spines touching each other during use of the catheter. The staggered electrode configuration provides the distal electrode assembly with a greater effective contact surface because the effective concentric electrode arrays is increased or at least doubled.

SUMMARY OF THE INVENTION

There is provided, in accordance with some embodiments of the present invention, an apparatus including a shaft, configured for insertion into a body of a subject, and an expandable element coupled to a distal end of the shaft. The expandable element includes multiple electrodes arranged in a hexagonal grid when the expandable element is expanded.

In some embodiments, a distance between each pair of adjacent ones of the electrodes is between 1 and 5 mm.

In some embodiments, the expandable element includes an assembly of parallel splines, and the electrodes are grouped into rows coupled to the splines, respectively, the rows being staggered with respect to each other such that the electrodes are arranged in the hexagonal grid.

In some embodiments, each of the electrodes includes a ring fitted over a respective one of the splines.

In some embodiments, the expandable element includes a plurality of looped elements, each of which includes a different respective pair of the splines.

In some embodiments, the expandable element includes at least one rollable substrate, and the electrodes are coupled to the substrate such that the electrodes are arranged in the hexagonal grid when the substrate is unrolled.

In some embodiments, the substrate includes a printed circuit board (PCB).

In some embodiments, the expandable element includes an inflatable balloon, and the electrodes are coupled to the balloon such that the electrodes are arranged in the hexagonal grid when the balloon is inflated.

There is further provided, in accordance with some embodiments of the present invention, a method including inserting a shaft into a body of a subject. The method further includes, subsequently to inserting the shaft, expanding an expandable element coupled to a distal end of the shaft and including multiple electrodes arranged in a hexagonal grid when the expandable element is expanded. The method further includes, using the electrodes, acquiring electrical signals from tissue of the subject.

There is further provided, in accordance with some embodiments of the present invention, a method including obtaining a plurality of bipolar signals between respective pairs of electrodes contacting tissue of a subject, the electrodes being arranged in a hexagonal grid. The method further includes, based on the bipolar signals, computing an estimated path of bioelectrical propagation along the tissue.

In some embodiments, obtaining the bipolar signals includes:
  measuring respective unipolar signals from the electrodes; and
  obtaining each one of the bipolar signals by subtracting a respective pair of the unipolar signals from one another.

In some embodiments, the estimated path includes multiple linear segments, each of which passes between a respective one of the pairs of electrodes.

In some embodiments, the electrodes belong to an expandable element coupled to a distal end of a shaft disposed within a body of the subject.

BRIEF DESCRIPTION OF THE DRAWINGS

The present invention will be more fully understood from the following detailed description of embodiments thereof, taken together with the drawings, in which.

DETAILED DESCRIPTION OF EMBODIMENTS

Overview

Conventionally, a rectangular grid of electrodes is used to estimate a path of bioelectrical propagation along intrabody tissue, such as intracardiac tissue. However, a rectangular grid provides limited accuracy, due to the fact that each electrode in the grid has, at most, four nearest neighbors.

Hence, embodiments of the present invention provide a hexagonal grid of electrodes, in which each electrode has up to six nearest neighbors. To facilitate deploying and using the hexagonal grid, the hexagonal grid is coupled to an expandable element, comprising, for example, a rollable substrate, an inflatable balloon, or an assembly of splines. Following the expansion of the expandable element, the hexagonal grid is pressed against the tissue, and bipolar signals between pairs of the electrodes are obtained. Based on the bipolar signals, a processor computes an estimated path of bioelectrical propagation.

SYSTEM DESCRIPTION

Figure 1:
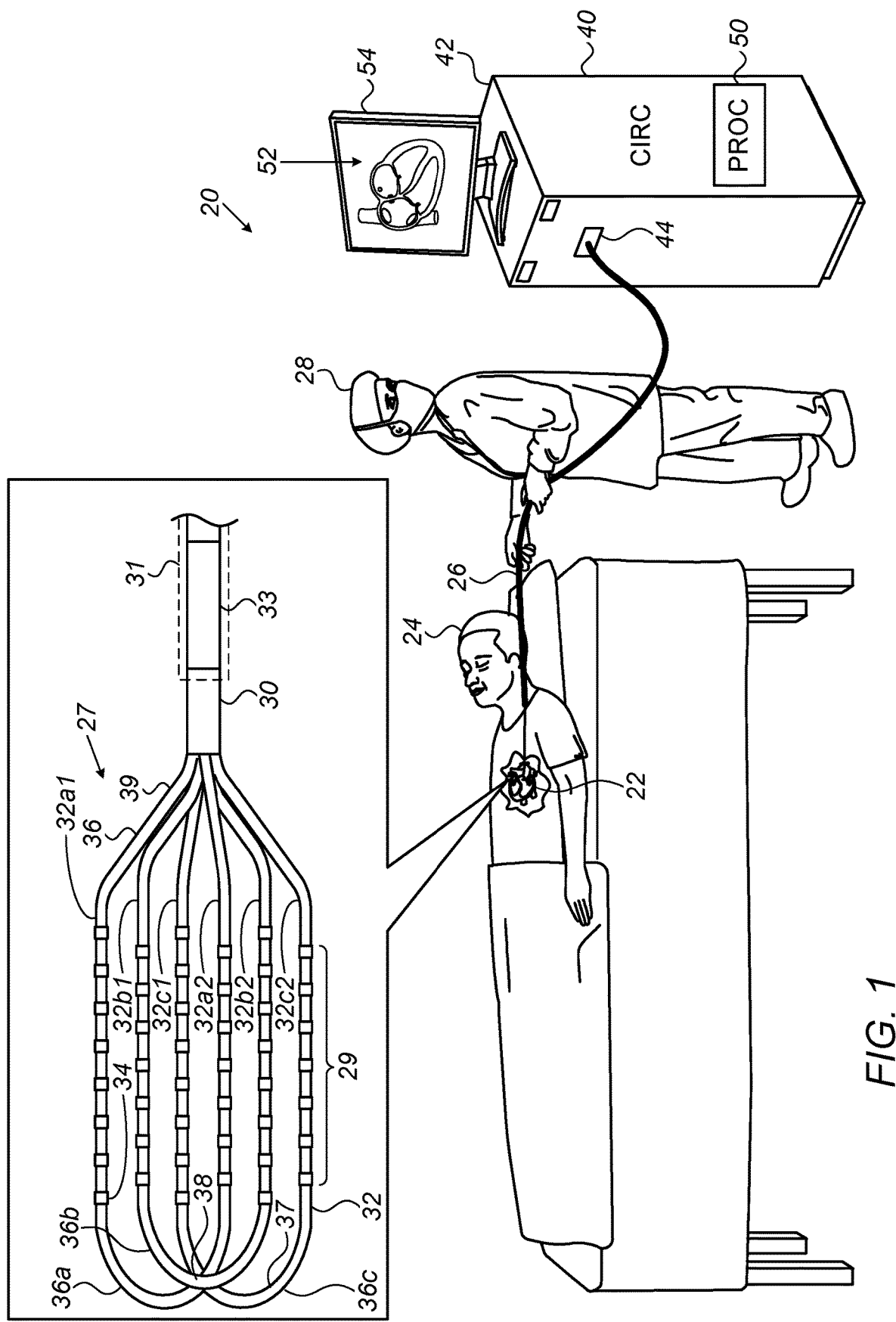
FIG. 1 is a schematic illustration of an electrophysiological mapping system, in accordance with some embodiments of the present invention.

Reference is initially made to FIG. 1, which is a schematic illustration of an electrophysiological mapping system 20, in accordance with some embodiments of the present invention.

System 20 comprises an intrabody probe 26, comprising a shaft 30 configured for insertion into a body of a subject 24. Probe 26 further comprises an expandable element 27 coupled to the distal end of the shaft. Expandable element 27 comprises multiple electrodes 34 arranged in a hexagonal grid when the expandable element is expanded (i.e., when the expandable element is in its expanded configuration). Electrodes 34 may be made of gold, platinum, palladium, and/or any other suitable metal or metallic alloy.

To perform an electrophysiological mapping, a physician 28 first inserts probe 26 into the body of subject 24. Subsequently, physician 28 navigates the probe to the target portion of the body that is to be mapped, such as a chamber of the heart 22 of the subject. Subsequently, electrodes 34 are used to measure electrogram voltages across tissue of the subject.

In some embodiments, expandable element 27 is made from a shape-memory material, such as Nitinol. In such embodiments, the expandable element is self-expanding, in that the expandable element expands by virtue of the shape-memory effect. To deploy the expandable element, the probe is first inserted into, and navigated through, a sheath 31, the distal end of which is located at the target portion of the body. Subsequently to the distal end of the probe reaching the target portion of the body, sheath 31 is withdrawn from over the expandable element, such that, by virtue of the expandable element being made from the shape-memory material, the expandable element expands from a compressed configuration, which the expandable element assumes while inside of the sheath, to an expanded configuration.

In other embodiments (e.g., as described below with reference to FIG. 5), the expandable element is actively expanded from its compressed configuration to its expanded configuration, by application of electrical and/or mechanical energy.

In some embodiments, as shown in FIG. 1, the expandable element comprises an assembly of parallel splines 32, and the electrodes are coupled to splines 32. For example, each of the electrodes may comprise a ring fitted over a respective one of the splines. More specifically, the electrodes may be grouped into rows 29 coupled to the splines, rows 29 being staggered with respect to each other such that the electrodes are arranged in a hexagonal grid.

Typically, in such embodiments, the splines are coupled to one another such that, in the absence of any unusually large forces applied to the splines, the relative positions of the splines are fixed. For example, pairs of the splines may belong to different respective looped elements 36 that are coupled to each other at a distal junction 38. In particular, each looped element 36 may comprise a pair of splines, along with an arched portion 37 that runs between the respective distal ends of the splines and a pair of proximal portions 39 that couple the looped element to the inner wall of shaft 30 such that the looped element protrudes from the shaft. Typically, each looped element has a circular transverse cross-sectional shape.

For example, as shown in FIG. 1, the probe may comprise three looped elements: a first looped element 36a, which comprises splines 32a1 and 32a2, a second looped element 36b, which comprises splines 32b1 and 32b2, and a third looped element 36c, which comprises splines 32c1 and 32c2.

In some embodiments, the looped elements overlap each other, such that each spline is adjacent to one or two other splines belonging to other looped elements. For example, as shown in FIG. 1, looped elements 36a-c may overlap each other such that the splines are arranged in parallel to each other in the following sequence: 32a1, 32b1, 32c1, 32a2, 32b2, 32c2.

In other embodiments, the looped elements are arranged within each other. For example, looped elements 36a-c may be arranged within each other such that the splines are arranged in parallel to each other in the following sequence: 32a1, 32b1, 32c1, 32c2, 32b2, 32a2.

In some embodiments, the assembly of splines 32 is flat (i.e., the splines are coplanar with each other) when the assembly is expanded and in the absence of any force applied to the expandable element. Nonetheless, the assembly may be sufficiently compliant so as to curve when pressed against the tissue. Thus, advantageously, the assembly of splines may conform to the tissue such that all the electrodes contact the tissue simultaneously. In other embodiments, the assembly of splines has slight curvature even in the absence of any force applied to the expandable element.

System 20 further comprises circuitry (CIRC) 40, which is typically contained within a console 42. Circuitry 40 is connected to the proximal end of probe 26, e.g., via an electrical interface 44 in console 42 such as a port or socket. Circuitry 40 comprises a processor 50, configured to perform the functionality described below. Typically, the circuitry further comprises analog-to-digital (A/D) and digital-to-analog (D/A) conversion circuitry for interfacing between processor 50 and probe 26.

Wires running through probe 26 transfer electrical signals between electrodes 34 and circuitry 40. Based on measurements of electrogram voltages obtained from electrodes 34, the processor may construct an electrophysiological map 52 and, optionally, display map 52 on a display 54.

In some embodiments, probe 26 further comprises an electromagnetic sensor 33 coupled to the distal end of the shaft. In such embodiments, the location of the probe may be tracked by an electromagnetic tracking system. In particular, a magnetic field generated in the vicinity of the subject may induce, in sensor 33, a signal that varies with the location and orientation of the sensor. Based on this signal, processor 50 may ascertain the location and orientation of the probe, as described, for example, in U.S. Pat. Nos. 5,391,199, 5,443,489, and 6,788,967 to Ben-Haim, in U.S. Pat. No. 6,690,963 to Ben-Haim et al., in U.S. Pat. No. 5,558,091 to Acker et al., and in U.S. Pat. No. 6,177,792 to Govari, whose respective disclosures are incorporated herein by reference.

Alternatively or additionally to an electromagnetic tracking system, other types of tracking systems may be used to track the probe. For example, electric currents may be passed between electrodes 34 and one or more electrode patches on the body of subject 24. Based on the distribution of the currents and/or physiological impedances computed therefrom, processor 50 may ascertain the location of the probe. Methods for impedance-based location sensing are disclosed, for example, in U.S. Pat. Nos. 5,983,126, 6,456,864, and 5,944,022, whose respective disclosures are incorporated herein by reference. In addition, methods for utilizing a calibrated current-position map to ascertain the location of the probe based on the distribution of the currents are disclosed, for example, in U.S. Pat. No. 7,536,218 to Govari et al. and U.S. Pat. No. 8,456,182 to Bar-Tal et al., whose respective disclosures are incorporated herein by reference.

In some embodiments, probe 26 further comprises an irrigation tube (not shown), configured to deliver an irrigating fluid, such as saline, from console 42 to the distal end of the shaft. The irrigating fluid may inhibit the blood of subject 24 from clotting near expandable element 27, e.g., near the area in which proximal portions 39 are coupled to shaft 30.

In general, the functionality of processor 50 may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, processor 50 may be embodied as a programmed processor comprising, for example, a central processing unit (CPU). Program code, including software programs, and/or data may be loaded for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Although FIG. 1 relates mainly to heart electrograms, it is noted that embodiments of the present invention may also be applied to the acquisition of brain electrograms, e.g., during a neurosurgical procedure.

The Hexagonal Grid

Figure 2:
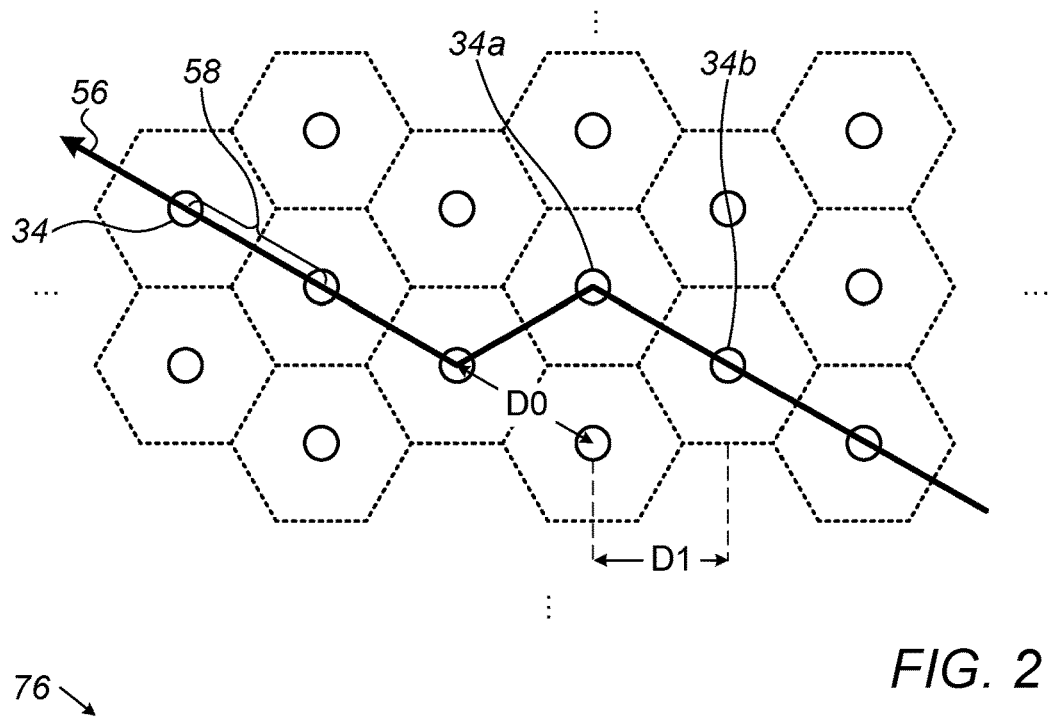
FIG. 2 is a schematic illustration of an arrangement of electrodes, in accordance with some embodiments of the present invention.

Reference is now made to FIG. 2, which is a schematic illustration of an arrangement of electrodes 34, in accordance with some embodiments of the present invention.

As described above with reference to FIG. 1, electrodes 34 are arranged in a hexagonal grid, which may also be referred to as a "close-packed pattern." In this arrangement, each electrode is located at the center of a respective hypothetical hexagon in a hexagonal grid (or "tessellation"). A distance D0, which is typically between 1 and 5 mm, separates each pair of adjacent (or "nearest-neighbor") electrodes from one another. In the context of the present application, including the claims, the distance between two elements refers to the distance between the respective centers of the elements. To achieve this arrangement for the embodiment of FIG. 1, successive electrodes on the same spline 32 are spaced apart from one another by distance D0, while adjacent splines are spaced apart from one another by a distance $$D1 = \frac{\sqrt{3}}{2} D0.$$

The hexagonal-grid arrangement illustrated in FIG. 2 has several advantages over a rectangular-grid arrangement.

First, by virtue of the rows of electrodes being staggered, there is less of a chance of electrodes 34 colliding with each other, e.g., when expandable element 27 (FIG. 1) is collapsed. Thus, there may be less noise added to the signals received from the electrodes.

Second, in the embodiment in which expandable element 27 comprises an assembly of splines as described above with reference to FIG. 1, the distance between each pair of adjacent electrodes lying on different respective splines is less sensitive to a change in distance between the splines, relative to a rectangular-grid arrangement. For example, supposing the distance between spline 32*a*1 and spline 32*b*1 (FIG. 1) increases by $x^*D1_0$, where $D1_0$ is the original distance between the two splines, the distance between any given electrode on spline 32*a*1 and each of its nearest neighbors on spline 32*b*1 would increase by only $$\left[ \frac{\sqrt{1+3(1+x)^2}}{2} - 1 \right] D0_0,$$

where $D0_0$ is the original distance between each pair of nearest neighbors. In contrast, with a rectangular-grid arrangement (in which D1=D0), the inter-electrode distance would increase by $x^*D0_0$.

Third, each of the electrodes, with the exception of those electrodes at the edges of the arrangement, has six nearest neighbors spaced equidistantly (at distance D0) from the electrode. In contrast, in a rectangular grid, each electrode has, at most, four such nearest neighbors. Thus, the hexagonal-grid arrangement facilitates obtaining a greater number of bipolar signals, where each bipolar signal represents, as a function of time, the voltage between a respective pair of nearest-neighbor electrodes.

Figure 3:
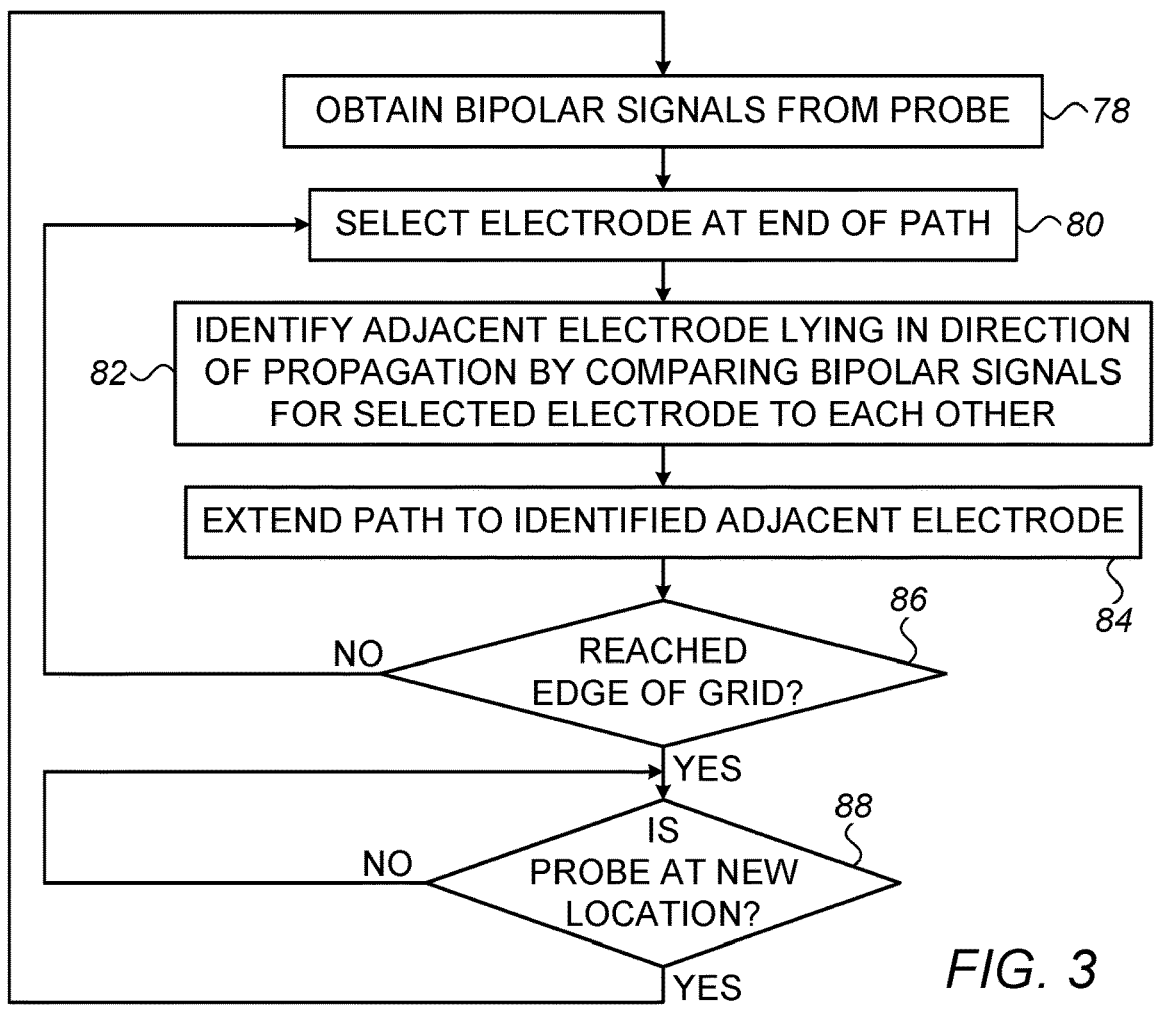
FIG. 3 is a flow diagram for an algorithm for computing an estimated path of bioelectrical propagation, in accordance with some embodiments of the present invention.

Aside from the intrinsic diagnostic benefit of obtaining a greater number of bipolar signals, the greater number of bipolar signals may provide greater accuracy in computing an estimated path 56 of bioelectrical propagation along the tissue of the subject. In this regard, reference is now additionally made to FIG. 3, which is a flow diagram for an algorithm 76 for computing path 56, in accordance with some embodiments of the present invention.

Per algorithm 76, processor 50 (FIG. 1) performs a signal-obtaining step 78 for each position of the probe. At signal-obtaining step 78, the processor obtains a plurality of bipolar signals from the probe, while the electrodes contact the tissue. In particular, the processor may obtain the bipolar signal between each electrode and each of its nearest neighbors. Thus, for example, for an electrode 34*a* shown in FIG. 2, the processor may obtain six bipolar signals.

In some embodiments, the processor measures each bipolar signal directly. In other embodiments, the processor measures a respective unipolar signal from each electrode, the unipolar signal representing, as a function of time, the voltage between the electrode and a common reference electrode. The processor then obtains each bipolar signal by subtracting the corresponding pair of unipolar signals from one another.

Subsequently, based on the bipolar signals, the processor computes at least a portion of path 56. In particular, the processor first selects the electrode that is currently at the end of the path, at an electrode-selecting step 80. Subsequently, at an adjacent-electrode-identifying step 82, the processor identifies the electrode that is adjacent to the selected electrode and that lies in the direction of the bioelectrical wavefront propagation (to the degree of precision provided by the hexagonal-grid arrangement). The identification of this adjacent electrode is performed by comparing the amplitudes, derivatives with respect to time, and/or any other properties of the bipolar signals for the selected electrode. For example, the processor may identify the adjacent electrode for which the amplitude or time-derivative of the bipolar signal is greatest. Subsequently, at a path-extending step 84, the processor extends the path to the identified adjacent electrode.

Thus, for example, the processor may identify that the wavefront is moving from an electrode 34b to electrode 34a. In response thereto, the processor may add, to path 56, a linear segment 58 between electrode 34b and electrode 34a.

Following path-extending step 84, the processor checks, at a first checking step 86, whether the path has reached the edge of the grid. If not, the processor returns to electrode-selecting step 80. Otherwise, the processor checks, at a second checking step 88, whether the probe is at a new location. Upon the probe reaching a new location, the processor returns to signal-obtaining step 78.

Thus, by virtue of the processor executing algorithm 76 (or any other suitable algorithm), path 56 may include multiple linear segments 58, each of which passes between a respective pair of electrodes. If the electrodes were arranged in a rectangular grid, there would be only four possible directions for each segment 58. Although it might be possible to compute an interpolated direction, such an interpolation might have limited accuracy, and/or might be computationally expensive. In contrast, given a hexagonal-grid arrangement, there are six possible directions for each segment 58. Thus, path 56 may be computed inexpensively and with greater accuracy. It is noted that, notwithstanding the above, the processor may compute interpolated directions even for a hexagonal-grid arrangement.

Subsequently to computing path 56, the processor may overlay the path on map 52 (FIG. 1) and/or on an image showing the position of the probe relative to the anatomy of the subject.

Alternate Embodiments

Figure 4:
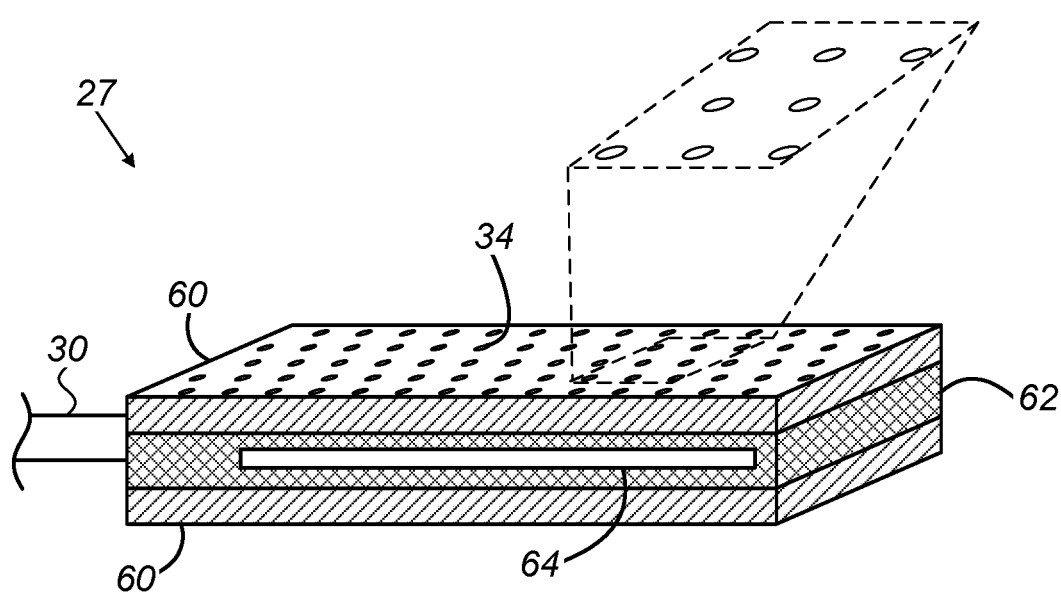
FIGS. 4-5 are schematic illustrations of expandable elements, in accordance with some embodiments of the present invention.

Reference is now made to FIG. 4, which is a schematic illustration of an alternate embodiment of expandable element 27, in accordance with some embodiments of the present invention.

In some embodiments, instead of an assembly of splines 32 (FIG. 1), expandable element 27 comprises at least one rollable substrate 60, and electrodes 34 are coupled to substrate 60 such that the electrodes are arranged in a hexagonal grid when the substrate is unrolled. Typically, substrate 60 comprises a printed circuit board (PCB), and the electrodes are printed onto the PCB. The substrate may be unrolled by withdrawing sheath 31 from over the expandable element, as described above with reference to FIG. 1.

For example, as described in U.S. patent application Ser. No. 16/852,165, whose disclosure is incorporated herein by reference, expandable element 27 may comprise a backing sheet 62, which may be made of a shape-memory material such as Nitinol. A single substrate may be coupled to one side of backing sheet 62; alternatively, two substrates may be coupled to different respective sides of backing sheet 62. An advantage of two substrates is that while the electrodes on one substrate acquire signals from the tissue, the electrodes on the other substrate may be used for cancelling any far-field signals. Optionally, the backing sheet may be shaped to define an irrigation channel 64, through which an irrigating fluid may flow.

In some embodiments, substrate 60, when unrolled and in the absence of any force applied to the expandable element, is flat, as shown in FIG. 4. Nonetheless, the expandable element may be sufficiently compliant so as to curve when pressed against the tissue. In other embodiments, the expandable element has slight curvature even in the absence of any force applied to the expandable element.

Figure 5:
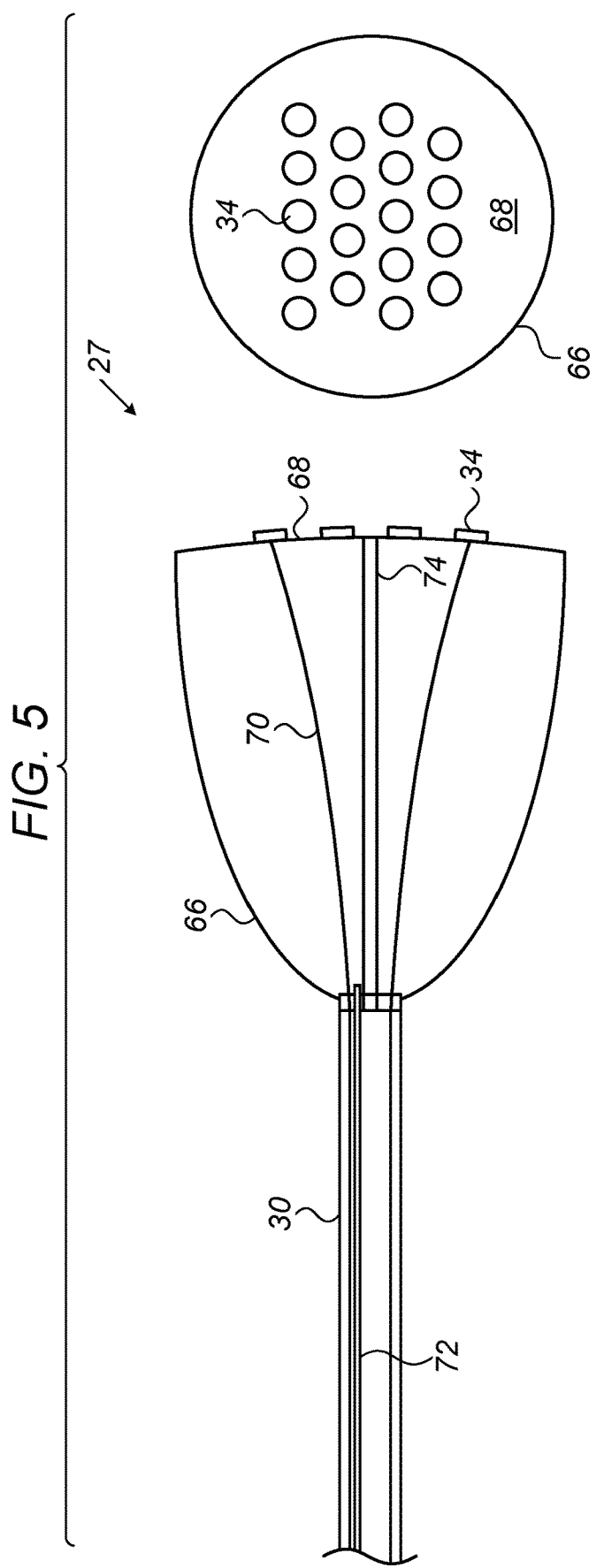

FIG. 5 shows yet another alternate embodiment, in which expandable element 27 comprises an inflatable balloon 66, and the electrodes are coupled to balloon 66 (e.g., to a distal surface 68 of the balloon) such that the electrodes are arranged in a hexagonal grid when the balloon is inflated. FIG. 5 shows both a side view and a frontal view of the balloon. Wires 70, which connect the electrodes to console 42 (FIG. 1), run through shaft 30 and balloon 66.

In general, the features of balloon 66 may be similar to those described in U.S. application Ser. No. 16/992,224, whose disclosure is incorporated herein by reference. For example, the balloon may be inflated by pumping a fluid into the balloon via an inflation tube 72. Optionally, the probe may be used with sheath 31 as described above with reference to FIG. 1, and the balloon may be inflated following the withdrawal of the sheath from over the balloon. A support rod 74, which is proximally coupled to shaft 30 and distally coupled to distal surface 68, may help stabilize the distal surface as the distal surface is pressed against the tissue. The electrodes may comprise respective PCBs; alternatively, the electrodes may be swaged onto the balloon, or coupled to the balloon using any other suitable technique.

In some embodiments, distal surface 68 is flat when the balloon is inflated and in the absence of any force applied to the balloon. Nonetheless, the distal surface may be sufficiently compliant so as to curve when pressed against the tissue. In other embodiments, the distal surface has slight curvature even in the absence of any force applied to the balloon, as shown in FIG. 5.

For each of the embodiments of FIGS. 4-5, the properties of the hexagonal grid of electrodes, as well as the manner in which the grid may be used, may be generally as described above with reference to FIGS. 2-3.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

We claim:

1. An apparatus for electrophysiological sensing, the apparatus comprising:
   a shaft, configured for insertion into a body of a subject; and
   an expandable element coupled to a distal end of the shaft and comprising multiple electrodes, the expandable element comprising an assembly of parallel splines, and wherein the electrodes are grouped into rows coupled to the splines, respectively, the rows being staggered with respect to each other, wherein successive electrodes on the same spline are spaced apart from one another by distance D0, while adjacent splines are spaced apart from one another by a distance $$\text{distance } D1 = \frac{\sqrt{3}}{2} D0$$

2. The apparatus according to claim 1, wherein the distance D0 is between 1 and 5 mm.

3. The apparatus according to claim 1, wherein each of the electrodes comprises a ring fitted over a respective one of the splines.

4. The apparatus according to claim 1, wherein the expandable element comprises a plurality of looped elements, each of which comprises a different respective pair of the splines.

5. The apparatus according to claim 1, wherein the electrodes are arranged in a hexagonal grid.

* * * * *